(12) United States Patent
Sharp et al.

(10) Patent No.: US 10,285,255 B2
(45) Date of Patent: May 7, 2019

(54) LASER ABLATION CELL AND INJECTOR SYSTEM FOR A COMPOSITIONAL ANALYSIS SYSTEM

(71) Applicant: Elemental Scientific Lasers, LLC, Omaha, NE (US)

(72) Inventors: Barry L. Sharp, Loughborough (GB); David N. Douglas, Plymouth (GB); Amy J. Managh, Bolton (GB)

(73) Assignee: ELEMENTAL SCIENTIFIC LASERS, LLC, Omaha, NE (US)

( * ) Notice: Subject to any disclaimer, the term of this patent is extended or adjusted under 35 U.S.C. 154(b) by 134 days.

(21) Appl. No.: 14/180,855

(22) Filed: Feb. 14, 2014

(65) Prior Publication Data

US 2014/0224775 A1 Aug. 14, 2014

Related U.S. Application Data

(60) Provisional application No. 61/764,976, filed on Feb. 14, 2013.

(51) Int. Cl.
*H05H 1/26* (2006.01)
*G01N 1/28* (2006.01)
(Continued)

(52) U.S. Cl.
CPC .............. *H05H 1/26* (2013.01); *G01N 1/28* (2013.01); *H01J 49/0463* (2013.01); *H05H 1/30* (2013.01)

(58) Field of Classification Search
CPC .............. G01N 1/28; H05H 1/26; H05H 1/30
(Continued)

(56) References Cited

U.S. PATENT DOCUMENTS

| 4,220,414 A | 9/1980 | Barringer |
| 4,575,609 A | 3/1986 | Fassel et al. |

(Continued)

FOREIGN PATENT DOCUMENTS

| JP | 08-005555 | 1/1996 |
| JP | 9-243535 A | 9/1997 |

(Continued)

OTHER PUBLICATIONS

Gschwind, et al., "Capabilities of inductively coupled plasma mass spectrometry for the detection of nanoparticles by carried monodisperse microdroplets," J. Anal. At. Spectrom. 26, Apr. 20, 2011, 1166-1174.

(Continued)

*Primary Examiner* — Dana Ross
*Assistant Examiner* — Ket D Dang
(74) *Attorney, Agent, or Firm* — Kevin E. West; Advent, LLP

(57) ABSTRACT

A laser ablation system includes a sample chamber 102 configured to accommodate a target 104 within an interior 106 thereof, a sample generator 108 configured to remove a portion of the target 104 (which may be subsequently captured as a sample) and an analysis system 110 configured to analyze a composition of the sample. A sample capture cell in the chamber proximate to the target has a capture cavity configured to receive target material, a first inlet configured to transmit a flow of a carrier gas from a first location adjacent to an exterior of the capture cell into a region of the capture cavity; and an outlet configured to receive carrier gas from another region of the capture cavity. The sample chamber 102 includes an injection nozzle 120 configured to introduce, into the interior 106, a fluid such as a carrier gas.

22 Claims, 6 Drawing Sheets

(51) Int. Cl.
*H05H 1/30* (2006.01)
*H01J 49/04* (2006.01)

(58) Field of Classification Search
USPC .......... 219/121.51, 121.5; 250/288; 204/603, 204/452; 118/726, 727, 730; 356/339, 356/336, 335, 337, 338, 340, 341, 342, 356/343, 246
See application file for complete search history.

(56) References Cited

U.S. PATENT DOCUMENTS

| | | | |
|---|---|---|---|
| 4,670,290 A * | 6/1987 | Itoh | B05B 7/226 219/121.5 |
| 5,432,601 A | 7/1995 | Tanaka et al. | |
| 5,504,327 A * | 4/1996 | Sproch | H01J 49/165 250/281 |
| 5,534,071 A | 7/1996 | Varshney et al. | |
| 5,537,206 A | 7/1996 | Akiyoshi et al. | |
| 5,725,153 A | 3/1998 | Wang et al. | |
| 5,884,846 A | 3/1999 | Tan | |
| 5,908,566 A * | 6/1999 | Seltzer | G01N 1/2258 219/121.36 |
| 6,166,379 A * | 12/2000 | Montaser | G01N 21/714 219/121.5 |
| 6,936,787 B2 * | 8/2005 | Tao | H05H 1/30 219/121.5 |
| 7,118,630 B1 * | 10/2006 | Balooch | C23C 14/0026 118/726 |
| 7,145,137 B2 | 12/2006 | Montaser et al. | |
| 7,572,999 B2 * | 8/2009 | Tao | G01N 30/7206 219/121.51 |
| 7,977,599 B2 * | 7/2011 | Adams | B23K 10/027 219/121.48 |
| 2004/0183008 A1 * | 9/2004 | Wiseman | G01N 21/73 250/288 |
| 2005/0195393 A1 | 9/2005 | Karanassios | |
| 2006/0024199 A1 | 2/2006 | Tao et al. | |
| 2009/0272893 A1 * | 11/2009 | Hieftje | H01J 49/0004 250/282 |
| 2009/0314753 A1 | 12/2009 | Kosmowski | |
| 2010/0207038 A1 | 8/2010 | Sharp et al. | |
| 2011/0089320 A1 | 4/2011 | Wiederin et al. | |
| 2011/0272386 A1 * | 11/2011 | Morrisroe | H05H 1/30 219/121.52 |
| 2013/0092533 A1 | 4/2013 | Sato et al. | |

FOREIGN PATENT DOCUMENTS

| | | | | |
|---|---|---|---|---|
| JP | 2003-215042 A | 7/2003 | | |
| JP | 2004-534241 A | 11/2004 | | |
| JP | 2006-38729 A | 2/2006 | | |
| JP | 2007-047185 A | 2/2007 | | |
| JP | 2008261758 A | 10/2008 | | |
| KR | 20050020603 A | * | 3/2005 | ............... B01L 3/04 |
| TW | 200837863 A | 9/2008 | | |
| TW | 201211291 A1 | 3/2012 | | |
| WO | WO94/17385 | 8/1994 | | |
| WO | 9517656 A1 | 6/1995 | | |
| WO | WO95/17656 A1 | 6/1995 | | |

OTHER PUBLICATIONS

Gurevich et al., A simple laser ICP-MS ablation cell with wash-out time less than 100 ms J. Anal. At. Spectrom., 22, Jul. 9, 2007, 1043-1050.

Lindner et al., Optimized Transport Setup for High Repetition Rate Pulse—Separated Analysis in Laser Ablationâ˜Inductively Coupled Plasma Mass Spectrometry. Anal. Chem., vol. 81, No. 11, Jun. 1, 2009, 4241-4248.

PCT/US2014/016085 International Search Report and Written Opinion dated Jul. 22, 2014, 16 pages.

Tanner et al., "In torch laser ablation sampling for inductively coupled plasma mass spectrometry" J. Anal. At. Spectrom. 20, Jul. 1, 2005, 987-989.

English translation of the May 17, 2016 Office action concerning Taiwanese Patent Application No. 103104712 which corresponds with the subject U.S. Appl. No. 14/180,855.

English translation of the Jun. 2, 2017 Office action concerning Chinese Patent Application No. 201480008569.0. 13 pages.

European Search Report dated Sep. 9, 2016 concerning European Patent Application No. EP14751410. 8 pages.

Arrowsmith, et al., "Entrainment and Transport of Laser Ablated Plumes for Subsequent elemental Analysis", Applied Spectroscopy, vol. 42, No. 7, 1988, 10 pages.

English translation of the Aug. 22, 2017 Office action concerning Japanese Patent Application No. 2015-558111, 10 pages.

English translation of the Sep. 26, 2017 Office action concerning Taiwanese Patent Application No. 103104709, 7 pages.

Search Report dated Aug. 30, 2018 for Taiwan Patent Application No. 107110312 filed Mar. 26, 2018.

* cited by examiner

LASER ABLATION CELL AND INJECTOR SYSTEM FOR A COMPOSITIONAL ANALYSIS SYSTEM

RELATED APPLICATIONS

This application claims benefit of U.S. Provisional Patent Application No. 61/764,976, filed on 14 Feb. 2013, which application is incorporated by reference as if fully set forth herein. This application also claims priority to PCT/US14/16085 filed on 12 Feb. 2014, which application is incorporated by reference as if fully set forth herein.

BACKGROUND

Embodiments of the present invention exemplarily described herein relate generally to apparatuses and methods for handling target material ejected or otherwise generated from a laser ablation site of a target (e.g., the form of particles and/or vapor). More particularly, embodiments of the present invention relate to apparatuses and methods for efficiently capturing target material, for efficiently transporting a sample containing the target material and for efficiently injecting a sample containing the target material into a sample preparation system. Embodiments of the present invention exemplarily described herein also relate generally to an apparatus for handling a target within a sample chamber. More particularly, embodiments of the present invention relate to apparatuses and methods for adjusting the position of a target holder with reduced lag and motion hysteresis.

Laser ablation Inductively Coupled Plasma Mass Spectrometry (LA-ICP-MS) or Laser ablation Inductively Coupled Plasma Optical Emission Spectrometry (LA-ICP-OES) techniques can be used to analyze the composition of a target (e.g., a solid or liquid target material). Often, a sample of the target is provided to an analysis system in the form of an aerosol (i.e., a suspension of solid and possibly liquid particles and/or vapor in a carrier gas, such as helium gas). The sample is typically produced by arranging the target within a laser ablation chamber, introducing a flow of a carrier gas within the chamber, and ablating a portion of the target with one or more laser pulses to generate a plume containing particles and/or vapor ejected or otherwise generated from the target (hereinafter referred to as "target material"), suspended within the carrier gas. Entrained within the flowing carrier gas, the target material is transported to an analysis system via a transport conduit to an ICP torch where it is ionized. A plasma containing the ionized particles and/or vapor is then analyzed by an analysis system such as an MS or OES system.

Conventional techniques such as LA-ICP-MS and LA-ICP-OES, however, are undesirably slow to carry out high-resolution compositional analysis (i.e., "imaging") of a target within a reasonable time frame. For example, current techniques undesirably take up to about 278 hours to image an area of 100 mm$^2$ at a pixel resolution of 10 μm. In addition, current techniques such as LA-ICP-MS and LA-ICP-OES are also not sensitive enough for high-resolution imaging or analysis of micron-sized and sub-micron side particles (e.g., nanoparticles). Example embodiments disclosed herein address these and other problems associated with conventional compositional analysis techniques.

DETAILED DESCRIPTION OF THE ILLUSTRATED EMBODIMENTS

Figure 1:
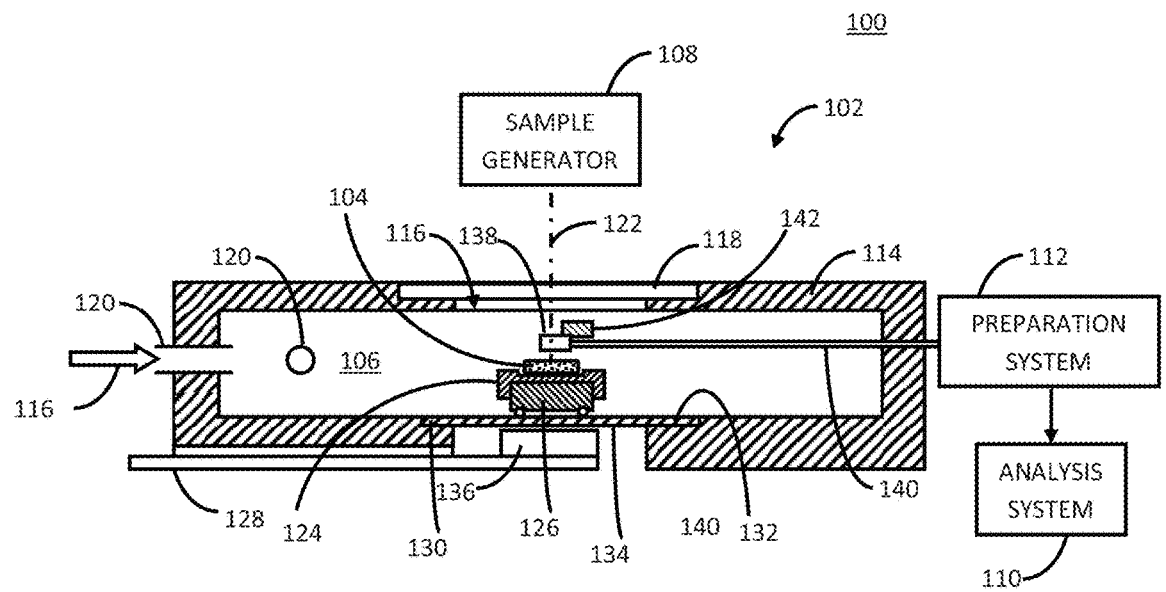
FIG. 1 schematically illustrates one embodiment of an apparatus for handling a target and for handling target material ejected from or otherwise generated from the target, and includes a cross-sectional view of a sample chamber, a sample capture cell and a target holder.

Example embodiments are described below with reference to the accompanying drawings. Many different forms and embodiments are possible without deviating from the spirit and teachings of the invention and so the disclosure should not be construed as limited to the example embodiments set forth herein. Rather, these example embodiments are provided so that this disclosure will be thorough and complete, and will convey the scope of the invention to those skilled in the art. In the drawings, the sizes and relative sizes of components may be exaggerated for clarity. The terminology used herein is for the purpose of describing particular example embodiments only and is not intended to be limiting. It is to be understood that various orientational terms such as "front" and "back" and "rear", "left" and "right", "top" and "bottom", "upper" and lower" and the like are used herein only for convenience, and not with the intention of limiting what is described to any absolute or fixed orientation relative to any environment in which any described structures may be used. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween.

FIG. 1 schematically illustrates one embodiment of an apparatus for handling a target and for handling target material ejected from or otherwise generated from the target, and includes a cross-sectional view of a sample chamber, a sample capture cell and a target holder.

Referring to FIG. 1, an apparatus, such as apparatus 100, for handling a target and for handling target material ejected from or otherwise generated from the target may include a sample chamber 102 configured to accommodate a target 104 within an interior 106 thereof, a sample generator 108 configured to remove a portion of the target 104 (which may be subsequently captured as a sample) and an analysis system 110 configured to analyze a composition of the sample. Examples of materials that can be provided as a target 104 include, for example, archaeological materials, biological assay substrates and other biological materials, ceramics, geological materials, pharmaceutical agents (e.g., pills), metals, polymers, petrochemical materials, liquids, semiconductors, etc. The apparatus 100 may optionally include a sample preparation system 112 configured to excite (e.g., ionize, atomize, illuminate, heat, or the like or a combination thereof) one or more components of the sample before the sample is analyzed by the analysis system 110. As will be described in greater detail below, the sample preparation system 112 may include a plasma torch (e.g., an ICP torch), or the like. Further, the analysis system 110 may be provided as an MS system, an OES system, or the like.

The sample chamber 102 may include a frame 114 having an optical port 116 extending therethrough to permit optical communication between the sample generator 108 and the interior 106 of the sample chamber 102. Optionally, a transmission window 118 may be coupled to the frame 114 and to span the optical port 116. The transmission window 118 is typically formed of a material (e.g., quartz) that is at least substantially transparent to laser light generated by the sample generator 108. The transmission window 118 may also be sealed to the frame 114 to prevent dust, debris or other unwanted gases or other sources of contamination from entering into the interior 106 through the optical port 116. In one embodiment, the transmission window 118 is be sealed to the frame 114 also to prevent particles ejected from the target 104, vapor generated from the target 104, etc., (the particles, vapor, etc., being collectively referred to herein as "target material", which is removed from the target 104), carrier gas or other fluids present within the interior 106, from exiting the sample chamber 102 through the optical port 116. Although the frame is illustrated as a single, integrally-formed piece, it will be appreciated that the frame 114 may be formed of multiple components that are coupled together, as is known in the art.

The sample chamber 102 may further include one or more injection nozzles 120 each configured to introduce, into the interior 106, a fluid such as a carrier gas (e.g., helium, argon, nitrogen, or the like or a combination thereof) at a flow rate in a range from 20 mL/min to 1000 mL/min (e.g., in a range from 100 mL/min to 150 mL/min, or 125 mL/min, or thereabout). For example, each injection nozzle 120 may be inserted through a fluid port in the frame 114 and include an inlet configured to be fluidly coupled to a fluid source (e.g., a pressurized fluid source) outside the sample chamber 102 and an outlet exposed within the interior 106 the sample chamber 102. Seals (not shown) may be provided between frame and the injection nozzles 120 to fluidly isolate the interior 106 of the sample chamber 102 with the environment outside the sample chamber 102. Upon introducing a carrier gas into the interior 106, a flow of the carrier gas (also referred to herein as a "carrier gas flow") is generated within the interior 106. It will be appreciated that the velocity and direction of the carrier gas flow at different locations within the interior 106 can vary depending upon: the shape and size of the interior 106 of the sample chamber 102, the configuration of the one or more injection nozzles 120, the flow rate with which carrier gas is introduced into the interior 106 by any particular injection nozzle 120, or the like or a combination thereof. In one embodiment, the pressure within the interior 106 can be maintained (e.g., to a pressure less than or equal to 11 psi) by controlling the flow rate with which carrier gas is introduced into the interior 106.

The apparatus 100 may further include a target positioning system configured to adjust the position of the target 104 relative to the optical path 122. In one embodiment, the positioning system includes a target holder 124 configured to support the target 104, a carriage 126 configured carry the target holder 124, a base 130 configured to support the carriage 126 within the interior 106 and a positioning stage 128 configured to move the carriage 126. Although the target holder 124 and the carriage 126 are illustrated as separate, separatable components, it will be appreciated that the target holder 124 and the carriage 126 may be integrally formed. Optionally, a height-adjustment mechanism (not shown) such as a micrometer can be provided to adjust a position of the target holder 124 along a vertical direction (e.g., along the optical path 122) to ensure that the target 104 is arranged at a suitable or beneficial position within the interior 106.

The positioning stage 128 may be configured to linearly translate the carriage 126 along at least one direction (e.g., an X-direction, a Y-direction orthogonal to the X-direction, or the like or a combination thereof) relative to the optical path 122, or may be configured to rotate the carriage 126 relative to the optical path 122, or the like or a combination thereof. In one embodiment, the positioning stage 128 and the frame 114 may both rest on a common support surface such as a table (not shown). A portion of the frame 114 may be spaced apart from the support surface to define a stage-receiving space therebetween, and the positioning stage 128 may be disposed in the stage-receiving space.

The base 130 may include a first side 132 exposed within the interior 106 and a second side 134 opposite the first side 132. The base 130 may be coupled to the frame 114 so as to fluidly isolate the interior 106 of the sample chamber 102 with the environment outside the sample chamber 102. Thus, as exemplarily illustrated, the carriage 126 and the positioning stage 128 are disposed at opposite sides of the base 130. To facilitate movement and beneficial positioning of the target 104 within the interior 106, the carriage 126 is magnetically coupled to the positioning stage 128 through the base 130. For example, carriage 126 may include one or more magnets (not shown) arranged therein and the positioning stage 128 may include an end effector 136 having one or more magnets attached thereto. An orientation of the magnets within the carriage 126 and the end effector 136 may be selected to generate an attractive magnetic field extending between the end effector 136 and the carriage 126, through the base 130. It will be appreciated that the base 130 may be constructed in any suitable or beneficial manner to transmit a magnetic field of sufficient strength between the end effector 136 and the carriage 126. For example, the base 130 may be formed from a material such as a metal, a glass, a ceramic, a glass-ceramic, or the like. In one embodiment, the base 130 may include a material formed of fluorphlogopite mica in a matrix of borosilicate glass.

To facilitate movement of the carriage 126 across the first side 132 of the base 130, the first side 132 may have a relatively smooth surface (e.g., with a surface roughness, Ra, of about 0.4 μm to about 0.8 μm). In one embodiment, the positioning system may further include one or more bearings coupled to the carriage 126 and configured to contact the first side 132 of the base 130. Although the apparatus 100 is illustrated as including the target positioning system, it will be appreciated that the target positioning system may be omitted, modified or substituted for any other suitable or beneficial mechanism for adjusting the position of the target 104 relative to the optical path 122.

Constructed according to the various embodiments exemplarily described above, the target positioning system ensures repeatable lateral angular and positioning of the target 104 within the interior 106, with low movement lag and motion hysteresis.

The sample generator 108 is configured to direct laser light along an optical path 122, through the optical port 116 and into the interior 106 of the sample chamber 102 to impinge upon the target 104. The laser light may be directed along the optical path 122 as one or more laser pulses generated by one or more lasers. One or more characteristics of the laser pulses may be selected or otherwise controlled to impinge a region of the target 104 to ablate a portion of the target 104. Characteristics that may be selected or otherwise controlled may, for example, include wavelength (e.g., in a range from about 157 nm to about 11 μm, such as 193 nm, 213 nm, 266 nm, or the like), pulse duration (e.g., in a range from about 100 femtoseconds to about 25 nanoseconds), spot size (e.g., in a range from about 1 μm to about 9 mm, or the like), pulse energy, average power, peak power, temporal profile, etc. The sample generator 108 may also include laser optics (e.g., one or more lenses, beam expanders, collimators, apertures, mirrors, etc.) configured to modify laser light generated by one or more of the lasers. As used herein, a region of the target 104 that is impinged by a laser pulse is referred to as a "laser ablation site". Upon being ablated, target material is removed from a region of the target 104 located within or adjacent to the laser ablation site to form a plume containing the target material.

To facilitate handling of the target material (e.g., so that the composition of the target material can be analyzed at the analysis system 110) the apparatus 100 may include a sample capture cell 138 configured to capture the target material when it is arranged operably proximate to the target 104. Target material captured by the sample capture cell 138 is also herein referred to as a "sample" or a "target sample". The apparatus 100 may further include a transport conduit 140 configured to transport the sample to the sample preparation system 112. In the illustrated embodiment, the apparatus may include a cell support 142 coupled to the sample chamber 102 (e.g., at the frame 114) to fix the sample capture cell 138 within the interior 106.

In one embodiment, the aforementioned optional height-adjustment mechanism may be used to adjust the height of the target holder 124 (and, thus, the target 104) relative to the sample capture cell 138 to ensure that the sample capture cell 138 is operably proximate to the target 104. In another embodiment, a height adjustment mechanism such as a micrometer may be optionally provided to adjust a position of the sample capture cell 138 relative to the target 104 (e.g., along the optical path 122) to ensure that the sample capture cell 138 is arranged at a suitable or beneficial position within the interior 106. Thus, in addition to (or instead of) adjusting a position of the target 104 relative to the sample capture cell 138, the position of the sample capture cell 138 relative to the target 104 may be adjusted to ensure that the sample capture cell 138 is operably proximate to the target 104. In one embodiment the sample capture cell 138 is operably proximate to the target 104 when the sample capture cell 138 is spaced apart from the target 104 by a gap distance, d (see, e.g., FIG. 2) in a range from 0.01 mm to 1 mm (e.g., in a range from 0.05 mm to 0.2 mm, or in a range from 0.1 mm to 0.2 mm). It will be appreciated, however, that depending on factors such as the carrier gas flow velocity within a region of the interior 106 between the sample capture cell 138 and the target 104, the gap distance can be less than 0.01 mm or greater than 1 mm, and may even contact the target 104.

Figure 2:
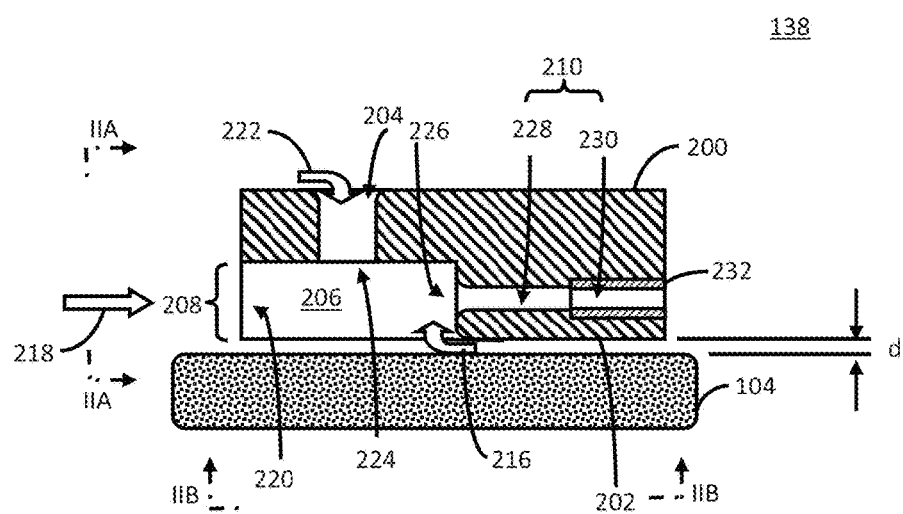
FIG. 2 is a cross-sectional view, taken along line II-II shown in FIG. 2A, schematically illustrating the sample capture cell shown in FIG. 1 according to one embodiment.
Figure 2A:
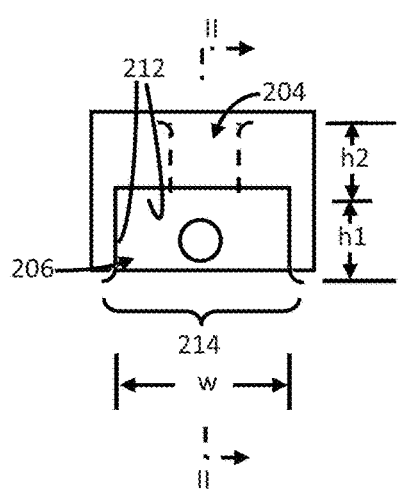
FIG. 2A is a plan view schematically illustrating a first inlet, a second inlet, a capture cavity and an outlet of the sample capture cell when viewed in the direction indicated along line IIA-IIA in FIG. 2.
Figure 2B:
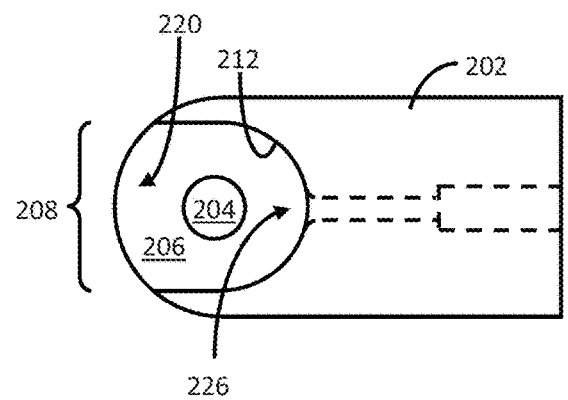
FIG. 2B is a plan view illustrating the first inlet, second inlet, capture cavity and outlet of the sample capture cell when viewed in the direction indicated along line IIB-IIB in FIG. 2.
Figure 3:
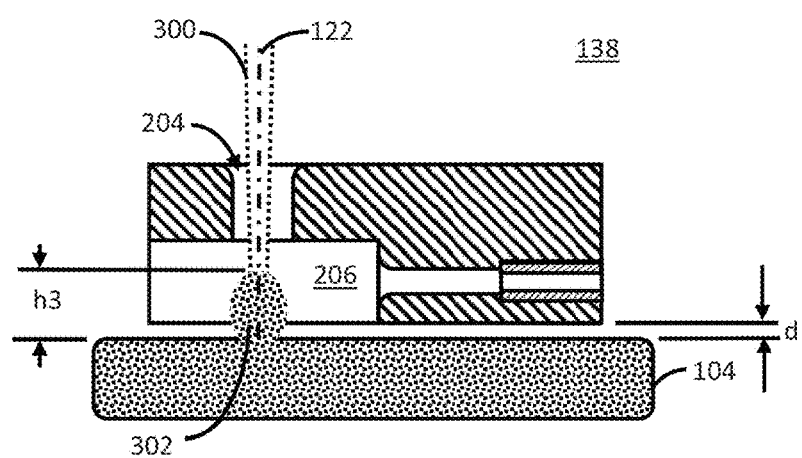
FIG. 3 is a cross-sectional view schematically illustrating laser light directed through the second inlet and capture cavity of the sample cell onto a target at a laser ablation site, and a resultant plume containing target material ejected from the target at the laser ablation site into the capture cavity of the sample cell.
Figure 4:
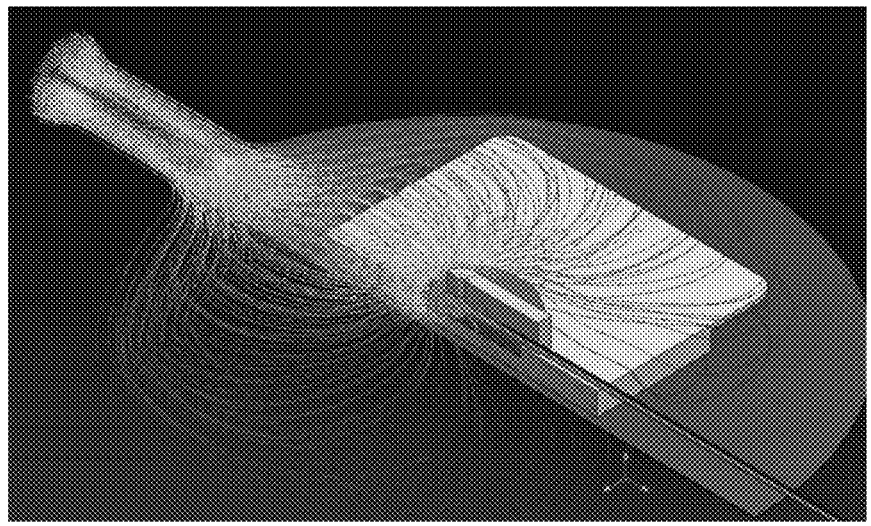
FIG. 4 is a perspective, cross-sectional view schematically illustrating characteristics of the flow of carrier gas within the interior of the sample chamber into the capture cavity of the sample capture cell shown in FIG. 2.
Figure 5:
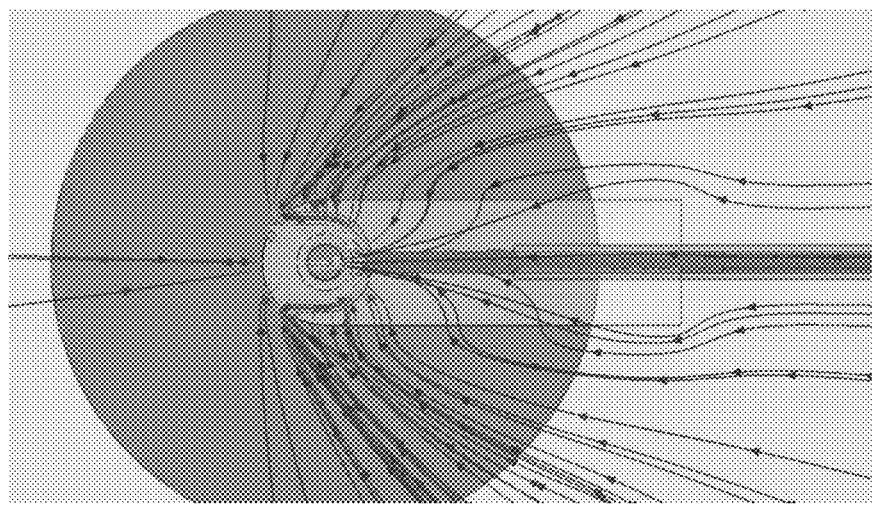
FIG. 5 is an enlarged, top plan view schematically illustrating the characteristics of the flow of carrier gas shown in FIG. 4 into the capture cavity of the sample capture cell shown in FIG. 2.
Figure 6:
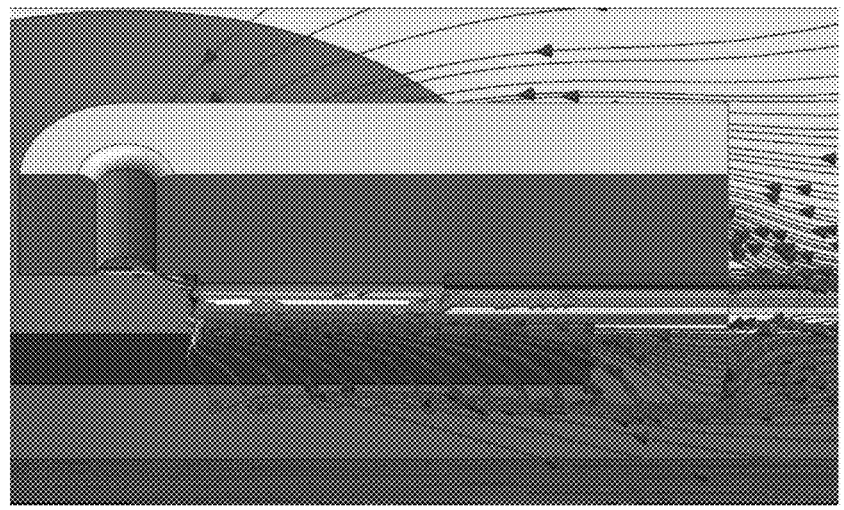
FIG. 6 is an enlarged perspective, cross-sectional view of the schematic shown in FIG. 4, schematically illustrating characteristics of the flow of carrier gas through an opening of the capture cavity and into the outlet of the sample capture cell shown in FIG. 2, from a region between the sample capture cell and the target.
Figure 7:
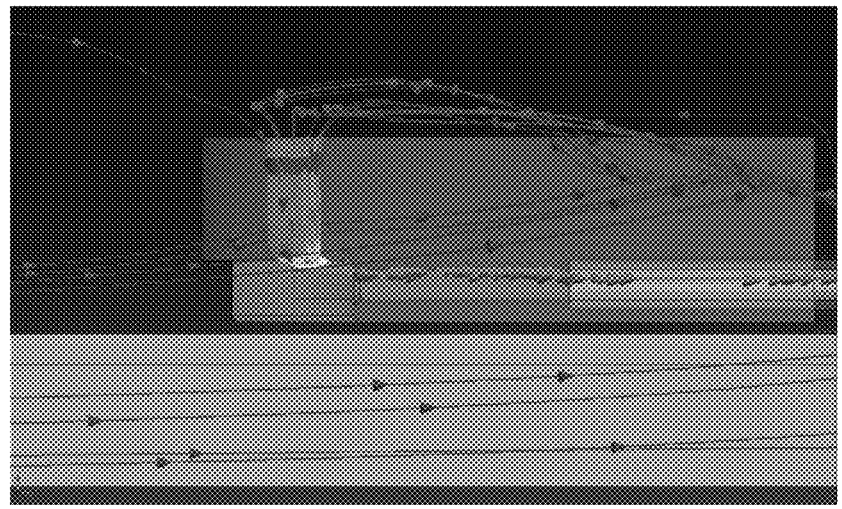
FIG. 7 is an enlarged side, cross-sectional view of the schematic shown in FIG. 4, schematically illustrating characteristics of the flow of carrier gas through the second inlet and into the outlet of the sample capture cell shown in FIG. 2.

FIG. 2 is a cross-sectional view, taken along line II-II shown in FIG. 2A, schematically illustrating the sample capture cell shown in FIG. 1 according to one embodiment. FIG. 2A is a plan view schematically illustrating a first inlet, a second inlet, a capture cavity and an outlet of the sample capture cell when viewed in the direction indicated along line IIA-IIA in FIG. 2. FIG. 2B is a plan view illustrating the first inlet, second inlet, capture cavity and outlet of the sample capture cell when viewed in the direction indicated along line IIB-IIB in FIG. 2. FIG. 3 is a cross-sectional view schematically illustrating laser light directed through the second inlet and capture cavity of the sample cell onto a target at a laser ablation site, and a resultant plume containing the target material from the laser ablation site into the capture cavity of the sample cell. FIG. 4 is a perspective, cross-sectional view schematically illustrating characteristics of the flow of carrier gas within the interior of the sample chamber into the capture cavity of the sample capture cell shown in FIG. 2. FIG. 5 is an enlarged, top plan view schematically illustrating the characteristics of the flow of carrier gas shown in FIG. 4 into the capture cavity of the sample capture cell shown in FIG. 2. FIG. 6 is an enlarged perspective, cross-sectional view of the schematic shown in FIG. 4, schematically illustrating characteristics of the flow of carrier gas through an opening of the capture cavity and into the outlet of the sample capture cell shown in FIG. 2, from a region between the sample capture cell and the target. FIG. 7 is an enlarged side, cross-sectional view of the schematic shown in FIG. 4, schematically illustrating characteristics of the flow of carrier gas through the second inlet and into the outlet of the sample capture cell shown in FIG. 2.

Referring to FIGS. 2, 2A and 2B, the sample capture cell 138 may generally be characterized as having an upper surface 200 (e.g., configured to generally face toward the sample generator 108) and a lower surface 202 (e.g., configured to generally face toward the target 104), a front end region and a back end region opposite the front end region. Generally, the sample capture cell 138 is arranged within the interior 106 such that the front end region is disposed upstream of the back end region, relative to the predominant direction of the carrier gas flow at the location in the interior 106 where the sample capture cell 138 is arranged. In one embodiment, a surface of the sample capture cell 138 defining the front end region is configured so as to be convexly-curved. For example, and as best shown in FIG. 2B, the surface of the sample capture cell 138 defining the front end region is circularly curved, centered on an axis of a second inlet 204 (discussed in greater detail below) with a radius in a range from 1.2 mm to 1.5 mm, or thereabout). It will be appreciated, however, that depending on factors such as the predominant direction of the carrier gas flow at the location in the interior 106 where the sample capture cell 138 is arranged, the location of the second inlet 204 within the sample capture cell 138, and other dimensions of the sample capture cell 138, the geometric configuration of the surface defining the front end region of the sample capture cell 138 may be varied in any manner that may be suitable or beneficial. It will further be appreciated that the location of the sample capture cell 138 within the interior 106 can be selected based upon factors such as the geometry of the interior 106, and the number and location of injection nozzles 120 generating the carrier gas flow within the interior 106. For example, if the interior 106 has a cylindrical geometry, and if only one injection nozzle 120 is used to introduce carrier gas into the interior 106 along the diameter of the cylindrical interior 106 at the aforementioned flow rate, then the sample capture cell 138 can be located at or near the center of the interior 106.

According to one embodiment, the sample capture cell 138 may further include a capture cavity 206, a first inlet 208 in fluid communication with the capture cavity 206, an outlet 210 in fluid communication with the capture cavity 206, and a guide wall 212 exposed within the capture cavity 206. In a further embodiment, the sample capture cell may further include the aforementioned second inlet 204 in fluid communication with the capture cavity 206. In one embodiment, the sample capture cell 138 can be provided as a monolithic body formed of any suitable material such as a glass, a ceramic, a polymer, a metal, or the like or a combination thereof. Moreover, two or more or all of the capture cavity 206, the first inlet 208, the second inlet 204, the outlet 210, and the guide wall 212, may be integrally formed within the body by conventional techniques (e.g., by machining, grinding, cutting, drilling, 3-D printing, etc.). In another embodiment, however, two or more or all of the capture cavity 206, the first inlet 208, the second inlet 204, the outlet 210, and the guide wall 212, may be separately formed from different components, which are subsequently coupled together.

The capture cavity 206 extends from an opening 214 formed in the lower surface 202 of the sample capture cell 138 and is configured to receive, through the opening 214, the plume containing the target material ejected or otherwise generated from the laser ablation site on the target 104 when the sample capture cell 138 is arranged operably proximate to the target 104. In an embodiment in which the sample capture cell 138 is spaced apart from the target 104, carrier gas adjacent to the target 104 can be also be transmitted into the capture cavity 206 through the opening 214. In the illustrated embodiment, the guide wall 212 defines the extent (e.g., lateral, vertical, etc.) of the capture cavity 206 within the sample capture cell 138. In one embodiment, the volume of the capture cavity 206 can be in a range from 0.001 $cm^3$ to 1 $cm^3$ (e.g., 0.005 $cm^3$, or thereabout). It will be appreciated, however, that depending on factors such as the carrier gas flow velocity within the region of the interior 106 where the sample capture cell 138 is located, the size of the plume of target material, etc., the volume of the capture cavity 206 can be less than 0.001 $cm^3$ or greater than 1 $cm^3$.

As best shown in FIGS. 2 and 2A, a transition region of the guide wall 212 extending from the lower surface 202 into the interior of the sample capture cell 138 is rounded or chamfered. By providing a rounded or chamfered transition region, the turbulence of a surface flow 216 of carrier gas entering into the capture cavity 206 from the a region near the surface of the target 104 through the opening 214 can be controlled to be suitably or beneficially small. In one embodiment, the round or chamfer of the transition region may have a radius of 0.1 mm, or thereabout. It will be appreciated, however, that depending on factors such as the carrier gas flow velocity within a region of the interior 106 between the sample capture cell 138 and the target 104 and the aforementioned gap distance, the radius of the transition region can be significantly more or less than 0.1 mm. A more detailed rendering of the flow of carrier gas into the capture cavity 206 via the opening 214 is exemplarily and schematically illustrated in FIGS. 4 and 6. In some embodiments, the sample capture cell 138 can be configured such that the surface flow 216 is sufficient to lift target material from the surface of the target 104 into the capture cavity 206 through the opening 214 (where, thereafter, it can be transferred into the outlet 210) when the sample capture cell 138 is operably proximate to the target 104.

The first inlet 208 extends from the capture cavity 206 to a surface of the sample capture cell 138 defining the front end region. Accordingly, the first inlet 208 is configured to transmit a primary flow 218 of the carrier gas from a first location adjacent to the front end region of the sample capture cell 138 into a first region 220 of the capture cavity 206, which is adjacent to the first inlet 208. A more detailed rendering of the flow of carrier gas through the first inlet 208 into the first region 220 of the capture cavity 206 is exemplarily and schematically illustrated in FIGS. 4 and 5. In the illustrated embodiment, the first inlet 208 extends vertically from the lower surface 202 toward the upper surface 200 to a height, h1 (see, e.g., FIG. 2A), of 1 mm (or thereabout), and extends horizontally between the lower surface 202 and upper surface 200 across a width, w (see, e.g., FIG. 2A), of 2.2 mm (or thereabout). It will be appreciated, however, that depending on factors such as the carrier gas flow velocity within a region of the interior 106 at the first location, the size and shape of any portion of the first inlet 208 (e.g., from the surface of the sample capture cell 138 defining the front end region to the capture cavity 206) may be modified in any suitable or beneficial manner. Constructed as exemplarily described above, the first inlet 208 is configured to transmit the primary flow 218 into the first region 220 of the capture cavity 206 along a first direction that is generally (or at least substantially) parallel to a surface of the target 104. Although, in the illustrated embodiment, the first inlet 208 extends from the lower surface 202 toward the upper surface 200, it will be appreciated that, in other embodiments, the first inlet 208 may be spaced apart from the lower surface 202. Although, in the illustrated embodiment, dimensions (e.g., height and width dimensions) of the first inlet 208 are illustrated as being the same as those of the capture cavity 206 at the first region 220, it will be appreciated that, in other embodiments, dimensions (e.g., height and width dimensions) of the first inlet 208 may be different from those of the capture cavity 206 at the first region 220.

The second inlet 204 extends from the capture cavity 206 to the upper surface 200 of the sample capture cell 138. Accordingly, the second inlet 204 is configured to transmit a secondary flow 222 of the carrier gas from a second location, adjacent to the upper surface 200 of the sample capture cell 138, into a second region 224 of the capture cavity 206. A more detailed rendering of the flow of carrier gas through the second inlet 204 into the second region 224 of the capture cavity 206 is exemplarily and schematically illustrated in FIG. 7. In the illustrated embodiment, the second inlet is a configured as a circular tube having a diameter in a range from 0.5 mm to 0.85 mm (or thereabout), aligned with and extending along the optical path 122 from the capture cavity 206 to the upper surface 200 so as to a height, h2 (see, e.g., FIG. 2A), of 2 mm (or thereabout). It will be appreciated, however, that depending on factors such as the carrier gas flow velocity within the interior 106 at the second location, the size and shape of any portion of the second inlet 204 (e.g., from the upper surface 200 of the sample capture cell to the capture cavity 206) may be modified in any suitable or beneficial manner.

As best shown in FIGS. 2 and 2A, a transition region of a wall extending from the upper surface 200 into the second inlet 204 is rounded or chamfered. By providing a rounded or chamfered transition region, the turbulence of the flow of carrier gas entering into the second inlet 204 can be controlled to be suitably or beneficially small. In one embodiment, the round or chamfer of the transition region may have a radius of 0.25 mm, or thereabout. Thus, the second inlet 204 may have a relatively large first diameter at the upper surface 200 and a relatively small second diameter at a location below the transition region (e.g., 0.85 mm, or thereabout). It will be appreciated, however, that depending on factors such as the carrier gas flow velocity within a region of the interior 106 over the upper surface 200 of the sample capture cell 138, the radius of the transition region can be significantly more or less than 0.25 mm.

Constructed as exemplarily described above, the second inlet 204 is configured to transmit the flow of the carrier gas into the second region 224 of the capture cavity 206 along a second direction that is generally (or at least substantially) perpendicular to a surface of the target 104. In another embodiment, however, the second inlet 204 may be configured to transmit the flow of the carrier gas into the second region 224 of the capture cavity 206 along a second direction that is substantially oblique to a surface of the target 104. Further, and as best shown in FIG. 3, the second inlet 204 is configured such that the sample generator 108 is in optical communication with a region of the target 104 (e.g., along the optical path 122) through the second inlet 204 and the capture cavity 206. Accordingly, laser light 300 may be directed from the sample generator 108 along the optical path 122, through the second inlet 204 and the capture cavity 206 to impinge upon the target 104 at a laser ablation site. When the directed laser light 300 impinges the target 104 at the laser ablation site, a plume 302 containing the target material ejected or otherwise generated from the target 104.

Depending on factors such as the material of the target 104, characteristics of the directed laser light 300, the velocity of the carrier gas flow, etc., vertical expansion of the plume may occur very rapidly. For example, the plume may extend to a height, h3 (see, e.g., FIG. 3) above the target 104 of about 2 mm within less than 0.5 ms (e.g., about 2 ms) after the directed laser light 300 impinges the target 104 at the laser ablation site. By transmitting a flow of the carrier gas through the second inlet into the third region via along the second direction, the vertical expansion of the plume may be prevented or otherwise minimally re-entrained, thereby reducing or minimizing the volume that the plume of target material would otherwise occupy within the capture cavity 206. By reducing or minimizing the volume that the plume of target material occupies within the capture cavity 206, target material within the can be efficiently captured and transferred into the outlet 210, as will be described in greater detail below.

The outlet 210 extends from a surface of the sample capture cell 138 defining the back end region to a region of the guide wall 212 exposed within the capture cavity 206. Accordingly, the outlet 210 is configured to receive carrier gas from a third region 226 of the capture cavity 206 so that the received carrier gas can be transmitted to a location outside the sample capture cell 138 (e.g., via the transport conduit 140). In the illustrated embodiment, the outlet 210 includes a first bore 228 having an inlet arranged at the third region 226 of the capture cavity 206, and a second bore 230 axially aligned with the first bore 228 and extending from the first bore 228 to the surface of the sample capture cell 138 defining the back end region. The first bore 228 and the second bore 230 are generally configured to accommodate a portion of the transport conduit 140. In the illustrated embodiment, the first bore 228 has a circular cross-section with a first diameter and the second bore 230 has a circular cross-section with a second diameter larger than the first diameter to additionally accommodate an outlet conduit seal 232. The first diameter may be equal to or slightly larger than the outer diameter of the transport conduit 140 (e.g., so that the transport conduit 140 may be inserted into the first bore 228), or may be less than or equal to the inner diameter of the transport conduit 140. In one embodiment, the first bore 228 may have a first diameter in a range from 0.5 mm (or thereabout).

As best shown in FIGS. 2 and 2B, a transition region of a wall extending from the guide wall 212 into the outlet 210 is rounded or chamfered. By providing a rounded or chamfered transition region, the turbulence of the flow of carrier gas entering into the outlet 210 can be controlled to be suitably or beneficially small. In one embodiment, the round or chamfer of the transition region may have a radius of 0.1 mm, or thereabout. Thus, the outlet 210 may have a relatively large diameter at the inlet of the first bore 228 (i.e., at the guide wall 212) (e.g., 0.82 mm, or thereabout) and a relatively small diameter at a location within an intermediate region of the first bore 228 (e.g., corresponding to the aforementioned first diameter of the first bore 228). It will be appreciated, however, that depending on factors such as the carrier gas flow velocity within the third region 226 of the capture cavity 206, the radius of the transition region can be significantly more or less than 0.1 mm.

The guide wall 212 is configured to deflect, vector or otherwise direct one or more flows of the carrier gas introduced into the capture cavity 206 (e.g., via one or more of the opening 214, the first inlet 208 and the second inlet 204) such that at least a portion of the plume of target material received within the capture cavity 206 through the opening 214 are entrained by the directed flow of carrier gas, thereby so as to be transferrable into the outlet 210 (see, e.g., FIG. 5). For purposes of discussion herein, target material transferred into the outlet 210 is "captured" by the sample capture cell 138 and, therefore, may also be referred to as a "sample" of the target 104 or as a "target sample". In one embodiment, the guide wall 212 is configured to direct the one or more flows of the carrier gas such that the flow of carrier gas into the plume 302 or into the outlet 210 is laminar or quasi-laminar. In another embodiment, however, the guide wall 212 is configured to direct the one or more flows of the carrier gas such that the flow of carrier gas into the plume 302 or into the outlet 210 is turbulent. Similarly, one or more of the aforementioned features of the sample capture cell 138 (e.g., the lower surface 202, the guide wall 212, the opening 214, the first inlet 208, the second inlet 204, or the like) may be configured such the flow of carrier gas over the surface of the target 104 and outside the capture cavity 206 is laminar, quasi-laminar, turbulent or a combination thereof.

As best shown in FIG. 2, the guide wall 212 is configured such that the inlet of the first bore 228 is recessed relative to a surface defining the front end region of the sample capture cell 138 by a distance of 2.5 mm (or thereabout). It will be appreciated, however, that depending on factors such as the carrier gas flow velocity within the capture cavity 206 and the location and orientation of the second inlet 204 within the sample capture cell 138, the distance by which the inlet of the first bore 228 is recessed relative to a surface defining the front end region of the sample capture cell 138 can be significantly more or less than 2.5 mm. As best shown in FIG. 2B, the guide wall 212 is configured so as to be curved in a region adjacent to the inlet of the first bore 228 (e.g., circularly curved, centered on an axis of the second inlet 204 with a radius in a range from 0.9 mm to 1.1 mm, or thereabout). It will be appreciated, however, that depending on factors such as the carrier gas flow velocity and direction within the capture cavity 206 and the location and orientation of the second inlet 204 within the sample capture cell 138, the geometric configuration may be varied in any manner that may be suitable or beneficial.

If the sample capture cell 138 is coupled to the transport conduit, the sample transferred into the outlet 210 can be transported to a location outside the sample capture cell 138 (e.g., via the transport conduit 140). To couple the transport conduit 140 to the sample capture cell 138, an end of the transport conduit 140 (also referred to as a "first end" or a "sample receiving end") is inserted into the second bore 230 and through the outlet conduit seal 232. Optionally, and depending upon the diameter of the first bore 228, the transport conduit 140 may be further inserted into the first bore 228. In one embodiment, the transport conduit 140 is inserted into the first bore 228 such that the sample receiving end is recessed within the first bore 228. For example, the sample receiving end can recessed within the first bore 228 to be spaced apart from the inlet of the first bore 228 by a distance in a range from 1 mm to 3 mm (or thereabout). In other embodiments, however, the transport conduit 140 is inserted into the first bore 228 such that the sample receiving end is recessed flush with, or extends beyond, the inlet of the first bore 228. Upon coupling the transport conduit 140 to the sample capture cell 138 in the manner described above, the carrier gas received at the outlet can also be received within the transport conduit 140 and transported to a location outside the sample chamber 102 (e.g., to the sample preparation system 112).

In addition to the sample receiving end, the transport conduit 140 may further include a second end (also referred to herein as a sample injection end) that is opposite the sample receiving end. Generally, the transport conduit 140 is at least substantially straight from the sample receiving end to the sample injection end, with a length (defined from the sample receiving end to the sample injection end) in a range from 20 mm to 2 m (e.g., in a range from 50 mm to 500 mm, or in a range from 100 mm to 600 mm, or in a range from 200 mm to 500 mm, or in a range from 200 mm to 450 mm, or thereabout) and an inner diameter in a range from 50 μm to 1 mm (e.g., in a range from 50 μm to 500 μm, or 250 μm, or thereabout). It will be appreciated, however, that depending on factors such as the pressure within the interior 106, the inner diameter of the transport conduit 140, the configuration of the sample chamber 102 and the sample preparation system 112, the length of the transport conduit 140 may be less than 20 mm or greater than 2 m. Similarly, depending on factors such as the pressure within the interior 106 and the length of the transport conduit 140, the inner diameter of the transport conduit 140 may be less than 50 μm or greater than 1 mm. The inner diameter of the transport conduit 140 at the sample receiving end may be same or different (i.e., larger or smaller) than the inner diameter of the transport conduit 140 at the sample injection end. Further, the inner diameter of the transport conduit 140 may be at least substantially constant along the length thereof, or may vary. In one embodiment, the transport conduit 140 is provided as a single, substantially rigid tube having no valves between the sample receiving end and sample injection end. Exemplary materials from which the transport conduit 140 can be formed include one or more materials selected from the group consisting of a glass, a polymer, a ceramic and a metal. In one embodiment, however, the transport conduit 140 is formed of fused glass. In another embodiment, the transport conduit 140 is formed of a polymer material such as a fluoropolymer (e.g., perfluoroalkoxy, polytetrafluoroethylene, or the like or a combination thereof), polyethylene terephthalate, or the like or a combination thereof. In yet another embodiment, the transport conduit 140 is formed of a ceramic material such as alumina, sapphire, or the like or a combination thereof. In still another embodiment, the transport conduit 140 is formed of a metal material such as stainless steel, copper, platinum, or the like or a combination thereof.

Constructed as exemplarily described above, the transport conduit 140 can efficiently transport a sample from the sample capture cell 138 to the sample preparation system 112. Efficient capture and transfer of a sample from a laser ablation site to the transport conduit 140, coupled with efficient transport of the sample from the sample capture cell 138 to the sample preparation system 112, can enable the analysis system 110 to generate signals (e.g., corresponding to the composition of target sample) that have relatively short peak widths (e.g., in a range from about 10 ms to about 20 ms (e.g., 12 ms, or thereabout), measured relative to a baseline where 98% of the total signal is observed within 10 ms) and correspondingly fast wash-out times. Generating signals having such relatively short peak widths and fast wash-out times, can help to facilitate high-speed and high sensitivity compositional analysis of the target 104. Similarly, depending on factors such as the pressure within the interior 106 and the length of the transport conduit 140, the inner diameter of the transport conduit 140, the peak width may be beneficially increased to 1 s or thereabout.

Figure 8:
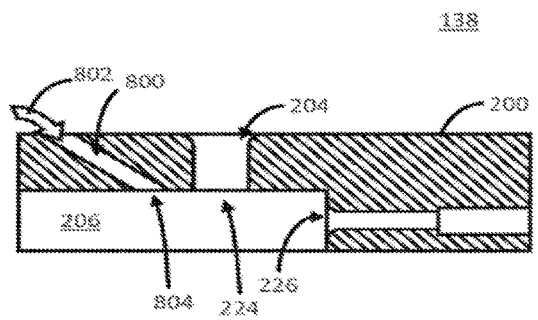
FIG. 8 is a cross-sectional view schematically illustrating the sample capture cell shown in FIG. 1 incorporating an auxiliary inlet, according to another embodiment.

FIG. 8 is a cross-sectional view schematically illustrating the sample capture cell shown in FIG. 1 incorporating an auxiliary inlet, according to another embodiment.

Referring to FIG. 8, the aforementioned sample capture cell may further include an auxiliary inlet, such as auxiliary inlet 800, extending from the capture cavity 206 to the upper surface 200 of the sample capture cell 138. Accordingly, the auxiliary inlet 800 is configured to transmit an auxiliary flow 802 of the carrier gas from a third location, adjacent to the upper surface 200 of the sample capture cell 138, into a fourth region 804 of the capture cavity 206. Upon being introduced into the fourth region 804, the auxiliary flow 802 may mix with the directed flow(s) of carrier gas present within the capture cavity 206 and, thereafter, transferred into the outlet 210. In the illustrated embodiment, the fourth region 804 is closer to the first region 220 than the third region 226. In other embodiments, however, the fourth region 804 may be closer to the third region 226 than the first region 220, or may be equidistant between the first region 220 and the third region 226.

In the illustrated embodiment, the auxiliary inlet is configured as a circular tube having a diameter equal to or different from (e.g., larger than or smaller than) the diameter of the second inlet. It will be appreciated, however, that depending on factors such as the carrier gas flow velocity within the interior 106 at the second location, the size and shape of any portion of the auxiliary inlet 800 (e.g., from the upper surface 200 of the sample capture cell to the capture cavity 206) may be modified in any suitable or beneficial manner. Although not illustrated, the auxiliary inlet may include a wall having a transition region extending from the upper surface 200 into the auxiliary inlet 800 and configured in the manner discussed above with respect to the second inlet 204. Constructed as exemplarily described above, the auxiliary inlet 800 is configured to transmit the auxiliary flow 802 into the fourth region 804 of the capture cavity 206 along a third direction that is for example, different from the aforementioned first direction and second direction. In one embodiment, the third direction may be substantially oblique, at least substantially parallel or at least substantially perpendicular to the surface of the target 104 when the sample capture cell 138 is operably proximate to the target 104.

Although the auxiliary inlet 800 is illustrated as being integrally formed within the body of the sample capture cell 138, it will be appreciated that the auxiliary inlet 800 may be separately formed from a different component, which is subsequently coupled to the body of the sample capture cell 138. Further, although the auxiliary inlet 800 is illustrated as transmitting the auxiliary flow 802 of carrier gas into the fourth region 804 of the capture cavity 206, the auxiliary inlet 800 may be positioned, oriented or otherwise configured to transmit the auxiliary flow 802 of carrier gas into the first region 220, the third region 226, or the second region 224 (e.g., the auxiliary inlet 800 may extend to the second inlet 204). In the illustrated embodiment, the auxiliary inlet 800 is configured to transmit the auxiliary flow 802 of carrier gas into the capture cavity 206 along a third direction that extends toward the outlet 210 and the target 104. In other embodiments, however, the third direction may extend toward the outlet 210 and away from the target 104, toward the first inlet 208 and the target 104, toward the first inlet 208 and away from the target 104, or the like or a combination thereof.

Although the auxiliary inlet 800 is described above as being configured to transmit the auxiliary flow 802 of carrier gas from the third location adjacent to the upper surface 200 of the sample capture cell 138 into the capture cavity 206, it will be appreciated that the auxiliary inlet 800 may be configured to transmit a flow of the carrier gas from any location adjacent to any surface of the sample capture cell 138. Moreover, although the auxiliary inlet 800 is described above as being configured to transmit a flow of carrier gas into the capture cavity 206, it will be appreciated that the sample capture cell 138 may be configured such that the auxiliary inlet 800 can be coupled to an external auxiliary fluid source (e.g., containing a fluid such as helium gas, argon gas, nitrogen gas, water vapor, atomized or nebulized fluids, atomized or nebulized solvents, discrete droplets containing microparticles, nanoparticles, or biological samples such as cells, or the like, or a combination thereof). In such a configuration, the auxiliary inlet 800 may transmit a fluid that is different from the carrier gas into the capture cavity 206, or may transmit an auxiliary flow of the carrier gas into the capture cavity 206, the auxiliary flow having a different characteristic (e.g., a different temperature, a different flow rate, etc.) from the carrier gas flow generated by the one or more injection nozzles 120. It will be appreciated that any fluid introduced into the capture cavity 206 by the auxiliary inlet 800 may mix with the directed flow(s) of carrier gas present within the capture cavity 206 and, thereafter, transferred into the outlet 210. In one embodiment, when coupled to an auxiliary fluid source, the auxiliary inlet 800 may transmit one or more fluids such as nitrogen gas or water vapor to facilitate sample counting, laser ablation standardization, calibration, or the like or a combination thereof.

Figure 9:
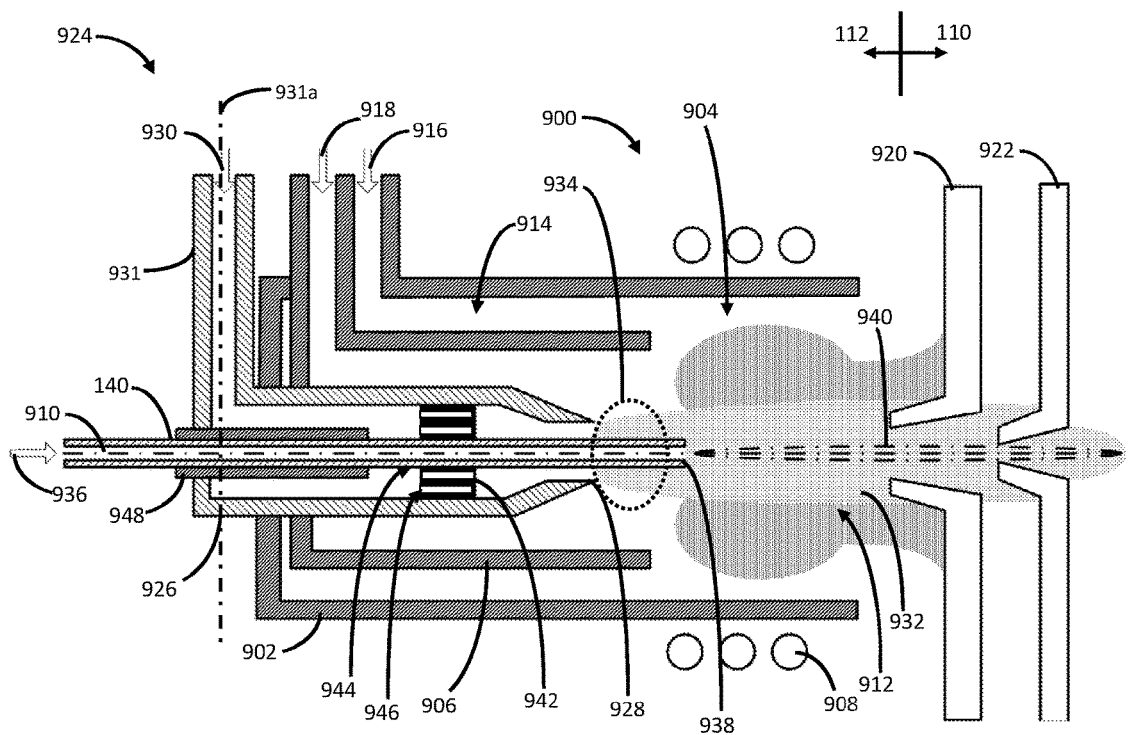
FIG. 9 is a cross-sectional view schematically illustrating one embodiment of an injector coupled to a sample preparation system, and a portion of an analysis system.

FIG. 9 is a cross-sectional view schematically illustrating one embodiment of an injector coupled to a sample preparation system, and a portion of an analysis system.

In the embodiment exemplarily illustrated in FIG. 9, the sample preparation system 112 may be provided as an ICP torch 900 including an outer tube 902 (also referred to herein as a "confinement tube 902") enclosing a space 904 where a plasma can be generated, an inner tube 906 (also referred to herein as a "plasma gas tube 906") arranged within the confinement tube 902, coaxial with an injection axis 910 of the confinement tube 902, and a coil 908 configured to ionize gas within the space 904 to generate a plasma 912 (e.g., occupying the darkly-shaded region within the space 904) when energized by an RF source (not shown). Although the sample preparation system 112 is illustrated as including a coil 908, it will be appreciated that the sample preparation system 112 may alternatively or additionally include ionization mechanisms of other configurations. For example, a set (e.g., a pair) of flat plates may be disposed outside the confinement tube 902 to ionize the plasma gas within the space 904 to generate the plasma.

In the illustrated embodiment, the confinement tube 902 and the plasma gas tube 906 are spaced apart from each other to define an annular outer gas transmission conduit 914 (also referred to as a "coolant gas transmission conduit") that may be coupled to a gas source (e.g., a reservoir of pressurized gas, not shown) to receive an outer flow 916 (also referred to as a "coolant flow") of gas (e.g., argon gas) and transmit the received outer flow 916 of gas into the space 904 (e.g., at a flow rate in a range from 10 L/min to 15 L/min, or thereabout). Gas introduced into the space 904 via the outer flow 916 can be ionized to form the aforementioned plasma 912. Generally, plasma 912 generated has a power of about 1.5 kW or less. In one embodiment, however, the plasma 912 generated can have a power higher than 1.5 kW (e.g., sufficient to melt the confinement tube 902). In such an embodiment, the gas introduced into the space 904 via the outer flow 916 can also be used to cool the confinement tube 902, preventing the confinement tube 902 from melting.

Optionally, the plasma gas tube 906 may be coupled to an auxiliary gas source (e.g., a reservoir of pressurized gas, not shown) to receive an intermediate flow 918 (also referred to as an "auxiliary flow") of gas (e.g., argon gas) and transmit the received intermediate flow 918 of gas into the space 904 (e.g. at a flow rate in a range from 1 L/min to 2 L/min). Gas introduced into the space 904 via the intermediate flow 918 can be used to adjust the position the base of the plasma 912 along the injection axis 910 relative to the confinement tube 902.

A portion of the plasma 912 generated within the space 904 is then transferred into the analysis system 110 (e.g., an MS system) by passing sequentially through an interface (e.g., an interface including a sampling cone 920 and a skimmer cone 922) of the analysis system 110. Although the analysis system 110 is illustrated as having an interface with the sampling cone 920 and the skimmer cone 922, it will be appreciated that the interface may be differently configured in any manner suitable or beneficial manner. If the aforementioned target material generated within the sample chamber 102 is introduced in the plasma generated within the space 904, then the target material may transferred into the analysis system 110 for compositional analysis.

To facilitate introduction of the sample through the transport conduit 140 into a sample preparation system such as sample preparation system 112, the apparatus 100 may include an injector, such as injector 924. The injector 924 may be detachably coupled to, or otherwise arranged operably proximate to, the sample preparation system 112 by any suitable or beneficial mechanism. In the illustrated embodiment, the injector 924 may include an outer conduit 926 having a fluid injection end 928, and the aforementioned transport conduit 140.

Generally, the outer conduit 926 is arranged within the plasma gas tube 906, coaxial with the injection axis 910 and is configured to be coupled to a fluid source (e.g., one or more reservoirs of pressurized gas, not shown) to receive an outer injector flow 930 of a fluid (e.g., argon gas). The outer injector flow 930 is conveyed by a port 931 (along an axis 931a) to a portion of the outer conduit 926 that extends from the fluid injection end 928 along the injection axis 910. As shown, the axis 931a is different from the injection axis 910. Fluid within the outer injector flow 930 is injectable into the space 904 through a fluid injection end 928 of the outer conduit 926. Generally, the inner diameter of the outer conduit 926 at the fluid injection end 928 is in a range from 1.5 mm to 3 mm (e.g., 2 mm, or thereabout). Upon injecting the fluid into the space 904 from the fluid injection end 928, a central channel 932 (e.g., occupying the lightly-shaded region within the space 904) can be formed within or "punched through" the plasma 912. Further, fluid injected into the space 904 through the fluid injection end 928 tends to generate a first zone 934 relatively close to the fluid injection end 928, which is characterized by a relatively high turbulence of fluid (e.g., including fluid from the outer injector flow 930 and possibly gas from the intermediate flow 918). Turbulence quickly decreases along the injection axis 910 with increasing distance from the fluid injection end 928 into the plasma 912. Accordingly, a second zone relatively distant from the fluid injection end 928 along the injection axis 910 and located within the central channel 932, can be characterized by a relatively low turbulence of fluid (e.g., including fluid from the outer injector flow 930 and possibly gas from the intermediate flow 918).

Generally, the transport conduit 140 configured to direct a carrier flow 936 containing the aforementioned target sample, along with any other fluids that carry the sample through the transport conduit 140 (e.g., the aforementioned carrier gas, any fluid introduced into the capture cavity 206 by the auxiliary inlet 800, or the like or a combination thereof) through the aforementioned sample injection end (indicated at 938). When directed through transport conduit 140 and past the sample injection end 938, the carrier flow 936 (and, thus, the sample contained therein) is injectable into the space 904 (e.g., along the injection axis 910), where it can be ionized and subsequently transferred to the analysis system 110.

In one embodiment, the transport conduit 140 may be arranged within the outer conduit 926, coaxial with the injection axis 910, such that the sample injection end 938 is locatable within the outer conduit 926, locatable outside the outer conduit 926, or a combination thereof. For example, the transport conduit 140 may be arranged within the outer conduit 926 such that the sample injection end 938 is located within the outer conduit 926, and is spaced away from the fluid injection end 928 by a distance in a range from 0 mm to 20 mm. In another example, transport conduit 140 may be arranged within the outer conduit 926 such that the sample injection end 938 is located outside the outer conduit 926, and is spaced away from the fluid injection end 928 by a distance in a range from greater than 0 mm to 15 mm (e.g., by a distance in a range from 6 mm to 12 mm, or by a distance in a range from 8 mm to 12 mm, or by a distance in a range from 10 mm to 12 mm, or by a distance of 12 mm, or thereabout). Depending on factors such as the configuration of the outer conduit 926, the flow rate of the outer injector flow 930 exiting the outer conduit 926, and the configuration of the sample preparation system 112, it will be appreciated that the sample injection end 938 may be located within the outer conduit 926 and spaced away from the fluid injection end 928 by a distance greater than 20 mm (or may be located outside the outer conduit 926 and spaced away from the fluid injection end 928 by a distance greater than 15 mm). The position of the transport conduit 140 may be fixed relative to the outer conduit 926, or may be adjustable.

In one embodiment, the relative position of the sample injection end 938 may be selected or otherwise adjusted to be positioned at a location (e.g., within the space 904) characterized by a fluid turbulence which is less that associated with the aforementioned first zone 934. For example, the sample injection end 938 may be positioned to be disposed within the aforementioned second zone. When the carrier flow 936 is injected from the sample injection end 938 when located within the second zone, lateral diffusion of the ionized target sample within the central channel 932 of the plasma 912 can be reduced significantly compared to the central channel 932 (e.g., as indicated by the relatively focused beam 940 of the ionized target sample). As a result, the beam 940 can be kept at least substantially on-axis relative to the interface of the analysis system 110 to enhance the sampling efficiency obtainable by the analysis system 110 and the sensitivity of the analysis system 110.

In one embodiment, the injector 924 may include a centering member 942 configured to maintain the radial position of the transport conduit 140 within the outer conduit 926. As exemplarily illustrated, the centering member 942 may be disposed within the outer conduit 926 and include a central bore 944 through which the transport conduit 140 can be inserted and a plurality of peripheral bores 946 disposed radially and circumferentially about the central bore 944 to permit transmission of the outer injector flow 930 from the aforementioned fluid source to the fluid injection end 928. In one embodiment, the injector 924 may further include a conduit guide 948 configured to help guide insertion of the transport conduit 140 into the centering member 942 from a location outside the injector 924. As shown in FIG. 9, the injector 924 does not include a heater configured to heat the fluid within the outer injector flow 930 transported by the outer conduit 926 and the carrier flow 936 (and, thus, the sample contained therein) transported in the transport conduit 140, respectively.

Constructed as exemplarily described above, the outer conduit 926 of the injector 924 may have the same primary function as a conventional ICP torch injector, in that it provides a fluid flow (e.g., Ar, or admixtures thereof with helium gas or nitrogen gas), that establishes the central channel of the plasma 912 into which the sample is introduced. In the injector 924 described above, the transport conduit 140 need not be coupled to the sample capture cell 138 as described above. In other such embodiments, the transport conduit 140 may alternatively or additionally be used to introduce a standard (e.g., to enable optimization of instrumental parameters, to enable calibration, etc.) into the analysis system 110 via a sample preparation system such as the sample preparation system 112, or the like. Such a standard could be introduced as an aerosol or dried aerosol (e.g. from a nebuliser, or as discrete droplets from a droplet generator, or as a gas or vapor generated by chemical or thermal means, etc.). The standard could even be an aerosol from a sample chamber other than the sample chamber 102. In other such embodiments, the transport conduit 140 may alternatively or additionally be used to introduce additional gases into the sample preparation system 112 (e.g. helium gas, nitrogen gas, water vapor derived for example from thermal vaporization or a nebulizer or droplet generator, etc.).

In one embodiment, the sample chamber 102 may be substituted or used in conjunction with a discrete droplet generator (e.g., derived from piezoelectric or thermal ink jet technologies, although any source of discrete droplets capable of delivering particles of less than 25 µm, or thereabout, to the sample preparation system 112 would work). In some applications, a continuous source of droplets, such as from a nebulizer, or continuous flow of vapor (e.g., water vapor). In such embodiments, the droplet generators may be coupled to a desolvation stage to carry out prior evaporation (which may be complete or partial) of the droplets. Droplet/desolvation technologies are well known and widely published.

In one embodiment, the droplet generator and accompanying desolvation unit may include two modes of operation. In a first mode of operation, the droplet generator and accompanying desolvation unit may replace the sample chamber 102 as the sample source, in which case a sample may be introduced directly into the transport conduit 140 of the injector 924 as a sequence of discrete droplets having diameters in the low or sub-micron range (after desolvation). These droplets may contain variously, for example, liquid samples, liquid droplets containing biological samples such as single cells, or micro or nano-particles. In a second mode of operation, the droplet generator and accompanying desolvation unit may run simultaneously and in synchronicity with the sample generator 108 and sample chamber 102 so that the liquid droplets can be introduced into the transport conduit simultaneously with the aerosol containing the target material, or sequentially in single or multiple events alternated with the aerosol containing the target material. This second mode of operation provides a mechanism for calibration (e.g., if the droplets contain standards), a mechanism for control of plasma conditions (e.g., if the droplets contain a solvent), or a mechanism for a quasi-continuous signal output that can be used for optimisation of instrumental parameters.

Figure 10:
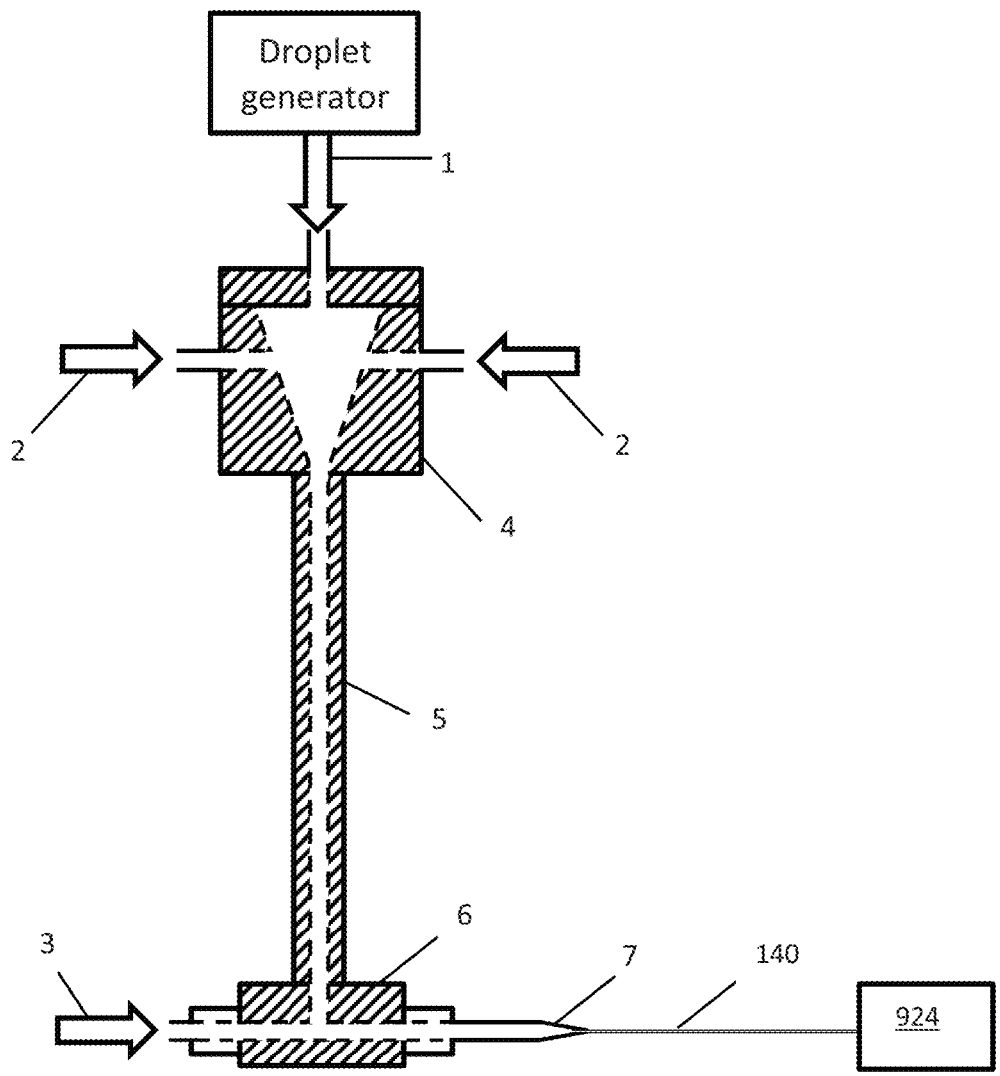
FIG. 10 is a partial cross-sectional view schematically illustrating one embodiment of a desolvation unit coupled between a droplet generator and an injector such as the injector shown in FIG. 9.

FIG. 10 is a partial cross-sectional view schematically illustrating one embodiment of a desolvation unit coupled between a droplet generator and an injector such as the injector shown in FIG. 9.

Referring to FIG. 10, the desolvation unit may include an adaptor 4 configured to receive a flow of droplets and/or vapor (e.g., as indicated at 1) and one or more desolvator gas flows (e.g., as indicated at 2) where the received droplet(s), vapor(s) and other gas flows can be mixed and thereafter be transported (e.g., vertically downwardly under the influence of gravity/and or the desolvating gas flow) through a tube 5 (e.g., a stainless steel tube) into a first inlet of an adaptor coupling 6, which may further include a second inlet configured to receive a flow of a make-up fluid (e.g., as indicated at 3). Within the adaptor coupling 6, the mixed droplet(s), vapor(s) and other gas flows are entrained by the flow of make-up fluid, transported through a tapered reducer 7 and into the transport conduit 140 and, thereafter, into the aforementioned injector 924. It will be appreciated that the taper provided by the tapered reducer 7 can be made sufficiently gradual to avoid introducing undesirable turbulence and particle loss.

Constructed as described above, the illustrated droplet generator and associated desolvation unit replace the sample chamber 102 and sample capture cell 138 discussed above. In another embodiment, however, the illustrated droplet generator and associated desolvation unit may be placed in-line with the sample chamber 102 and/or sample capture cell 138. In such an embodiment, an opening may be formed in the transport conduit 140 at a location between the sample receiving end (which is disposed within the sample chamber 102, coupled to the sample capture cell 138) and the sample injecting end 938 (which is disposed within the injector 924), and the adaptor coupling 6 may be coupled to the transport conduit 140 to place the tube 5 in fluid communication with the interior of the transport conduit 140.

The foregoing is illustrative of example embodiments of the invention and is not to be construed as limiting thereof. Although a few example embodiments have been described, those skilled in the art will readily appreciate that many modifications are possible without materially departing from the novel teachings and advantages of the invention. Accordingly, all such modifications are intended to be included within the scope of the invention as defined in the following claims.

What is claimed is:

1. An injector for injecting an aerosol sample into an inductively-coupled plasma (ICP) torch having a confinement tube, the injector comprising:

an outer conduit having a fluid input port and a fluid injection end in fluid communication with the fluid input port, wherein the fluid input port is configured to receive a first material flow containing a fluid and the outer conduit is configured to transport the first material flow from the fluid input port to the fluid injection end such that the fluid is injectable into the confinement tube from the fluid injection end; and a transport conduit disposed within the outer conduit and having a sample receiving end and a sample injection end, wherein the sample receiving end is configured to receive a second material flow containing an aerosol and the transport conduit is configured to transport the second material flow from the sample receiving end to the sample injection end such that the aerosol is injectable into the confinement tube from the sample injection end, the sample injection end having an inner diameter that is greater than or equal to 0.25 mm, wherein the transport conduit extends from the sample injection end along an injection axis, and a portion of the outer conduit extends along the injection axis, and a second portion of the outer conduit next to the fluid input port connects to the outer conduit extending along the injection axis from an axis that is different from the injection axis, and wherein the transport conduit is coaxial with the portion of the outer conduit that extends along the injection axis and the injector comprises only two conduits configured to transport a material flow, and wherein the fluid injection end of the outer conduit has an inner diameter that is smaller than the inner diameter of the outer conduit that extends along the injection axis and is in a range from 1.5 mm to 3 mm.

2. The injector of claim 1, wherein the sample injection end is located within the outer conduit.

3. The injector of claim 1, wherein the sample injection end is located outside the outer conduit.

4. The injector of claim 1, wherein an inner diameter of the sample receiving end is equal to the inner diameter of the sample injection end.

5. The injector of claim 1, wherein:

the outer conduit extends from the fluid injection end along the injection axis, the transport conduit extends from the sample injection end along the injection axis, and a distance between the fluid injection end and the sample injection end, when measured along the injection axis, is in a range from 0 mm to 20 mm.

6. The injector of claim 5, wherein the distance between the fluid injection end and the sample injection end, when measured along the injection axis, is in a range from 0 mm to 15 mm.

7. The injector of claim 1, wherein the transport conduit is at least substantially straight from the sample receiving end to the sample injection end.

8. The injector of claim 1, wherein the transport conduit extends from the sample injection end along the injection axis, wherein the outer conduit includes an interior surface, wherein the interior surface defines a space within which the first flow of material is transportable along the injection axis, wherein the outer conduit further includes a wall, wherein the interior surface of the outer conduit extends along the injection axis between the fluid injection end and the wall, and wherein the wall includes an opening through which the transport conduit is insertable, such that the transport conduit is disposed within the outer conduit.

9. The injector of claim 8, further comprising a conduit guide interposed between the wall and the transport conduit configured to help guide insertion of the transport conduit through the wall.

10. The injector of claim 9, wherein the conduit guide is spaced apart from the interior surface.

11. The injector of claim 1, wherein the sample injection end has an inner diameter that is greater than or equal to 0.5 mm.

12. The injector of claim 11, wherein the sample injection end has an inner diameter that is greater than or equal to 1 mm.

13. The injector of claim 1, wherein the transport conduit is axially movable within the outer conduit.

14. An apparatus, comprising:

the injector of claim 1 configured to be arranged operably proximate to a plasma torch configured to generate a plasma within a confinement tube thereof;

wherein the outer conduit of the injector is configured to generate, within the confinement tube, a first zone containing a first fluid flow having a relatively high turbulence and a second zone containing a second fluid flow having a relatively low turbulence, wherein the first zone is closer to the fluid injection end than the second zone; and the transport conduit of the injector has the sample injection end located within the second zone, wherein the transport conduit is configured such that the carrier flow containing material is injectable into the second zone from the sample injection end.

15. The apparatus of claim 14, wherein the sample injection end extends beyond the fluid injection end by a distance in a range greater than 1 mm.

16. An apparatus comprising:

a plasma torch defining a space within which a plasma is generatable; and the injector of claim 1, wherein the fluid through the outer conduit is injectable into the space from the fluid injection end and the aerosol through the transport conduit is injectable into the space from the sample injection end.

17. The apparatus of claim 16, wherein the plasma torch comprises an inductively coupled plasma (ICP) torch.

18. The apparatus of claim 16, further comprising a sample chamber having an interior configured to accommodate a target from which the aerosol is created.

19. The apparatus of claim 18, wherein the sample receiving end of the transport conduit is disposed within the sample chamber.

20. The apparatus of claim 19, further comprising a sample capture cell coupled to the sample receiving end of the transport conduit and configured to capture the aerosol and transfer the captured aerosol to the transport conduit.

21. The apparatus of claim 16, further comprising a droplet generator in fluid communication with an interior of the transport conduit, the droplet generator is configured to deliver particles into the interior of the transport conduit.

22. The apparatus of claim 21, further comprising a desolvation unit coupled between the droplet generator and the transport conduit.

* * * * *